(12) United States Patent
André et al.

(10) Patent No.: US 11,547,809 B2
(45) Date of Patent: Jan. 10, 2023

(54) MEDICAMENT DELIVERY DEVICE

(71) Applicant: CAREBAY EUROPE LTD, Sliema (MT)

(72) Inventors: Erika André, Sundbyberg (SE); Gerard Scanlon, Stockholm (SE)

(73) Assignee: SHL MEDICAL AG, Zug (CH)

(*) Notice: Subject to any disclaimer, the term of this patent is extended or adjusted under 35 U.S.C. 154(b) by 674 days.

(21) Appl. No.: 16/061,052

(22) PCT Filed: Nov. 7, 2016

(86) PCT No.: PCT/EP2016/076821
§ 371 (c)(1),
(2) Date: Jun. 11, 2018

(87) PCT Pub. No.: WO2017/102175
PCT Pub. Date: Jun. 22, 2017

(65) Prior Publication Data
US 2018/0353705 A1 Dec. 13, 2018

(30) Foreign Application Priority Data

Dec. 14, 2015 (SE) .................................. 1551636-2

(51) Int. Cl.
*A61M 5/20* (2006.01)
*A61M 5/32* (2006.01)
(Continued)

(52) U.S. Cl.
CPC ........ *A61M 5/3204* (2013.01); *A61M 5/2033* (2013.01); *A61M 5/3157* (2013.01);
(Continued)

(58) Field of Classification Search
CPC .. A61M 2005/2477; A61M 2005/2013; A61M 5/326; A61M 2005/206
See application file for complete search history.

(56) References Cited

U.S. PATENT DOCUMENTS

2012/0123350 A1* 5/2012 Giambattista ....... A61M 5/2033
604/198
2012/0209192 A1* 8/2012 Alexandersson ... A61M 5/3157
604/135
(Continued)

FOREIGN PATENT DOCUMENTS

CA 2359375 A1 7/2000
CN 102665801 A 9/2012
(Continued)

OTHER PUBLICATIONS

International Search Report and Written Opinion for Int. App. No. PCT/EP2016/076821, dated Jan. 30, 2017.

*Primary Examiner* — Emily L Schmidt
(74) *Attorney, Agent, or Firm* — McDonnell Boehnen Hulbert & Berghoff LLP

(57) ABSTRACT

A medicament delivery device is presented having a medicament container having an attached medicament delivery member; a housing where the medicament container is movable between a retracted and an extended position in which the medicament delivery member extends from the housing; a drive unit that advances the medicament container from its retracted position to its extended position to expel the contents through the medicament delivery member; and a medicament container holder for carrying the medicament container as it is advanced, the medicament container holder having a proximal end through which the medicament delivery member extends and a holding member releasably connected to the drive unit and attached to the medicament container holder. The holding member has a biasing element having a resilient structure in the form of a tubular wall provided with slots extending in the generally (Continued)

circumferential direction arranged to bias the medicament container in the proximal direction in the medicament container holder.

19 Claims, 12 Drawing Sheets

(51) Int. Cl.
    *A61M 5/315*     (2006.01)
    *A61M 5/24*     (2006.01)

(52) U.S. Cl.
    CPC ....... *A61M 5/326* (2013.01); *A61M 2005/206* (2013.01); *A61M 2005/2013* (2013.01); *A61M 2005/2477* (2013.01); *A61M 2005/3247* (2013.01); *A61M 2205/581* (2013.01)

(56) References Cited

U.S. PATENT DOCUMENTS

| | | | | |
|---|---|---|---|---|
| 2013/0226082 | A1* | 8/2013 | Klintenstedt | A61M 5/00 604/93.01 |
| 2013/0289491 | A1* | 10/2013 | Kramer | A61M 5/30 604/198 |
| 2015/0182691 | A1 | 7/2015 | McLoughlin | |
| 2015/0335824 | A1 | 11/2015 | Nzike et al. | |

FOREIGN PATENT DOCUMENTS

| | | |
|---|---|---|
| CN | 103167889 A | 6/2013 |
| CN | 102099069 B | 11/2013 |
| CN | 103764207 A | 4/2014 |
| CN | 105025954 A | 11/2015 |
| DE | 102008006300 A1 | 8/2009 |
| EP | 1349590 B1 | 10/2003 |
| JP | 2013-507173 A | 3/2013 |
| JP | 2013542807 A | 11/2013 |
| TW | 201417853 A | 5/2014 |
| TW | 201431577 A | 8/2014 |
| TW | 201503923 A | 2/2015 |
| TW | 201509458 A | 3/2015 |
| TW | 201509467 A | 3/2015 |
| TW | 201521808 A | 6/2015 |
| WO | 2005/044348 A1 | 5/2005 |
| WO | 2006/021932 A1 | 3/2006 |
| WO | 2011/043714 A1 | 4/2011 |
| WO | 2012/064258 A1 | 5/2012 |
| WO | 2015/11787 A1 | 1/2015 |

* cited by examiner

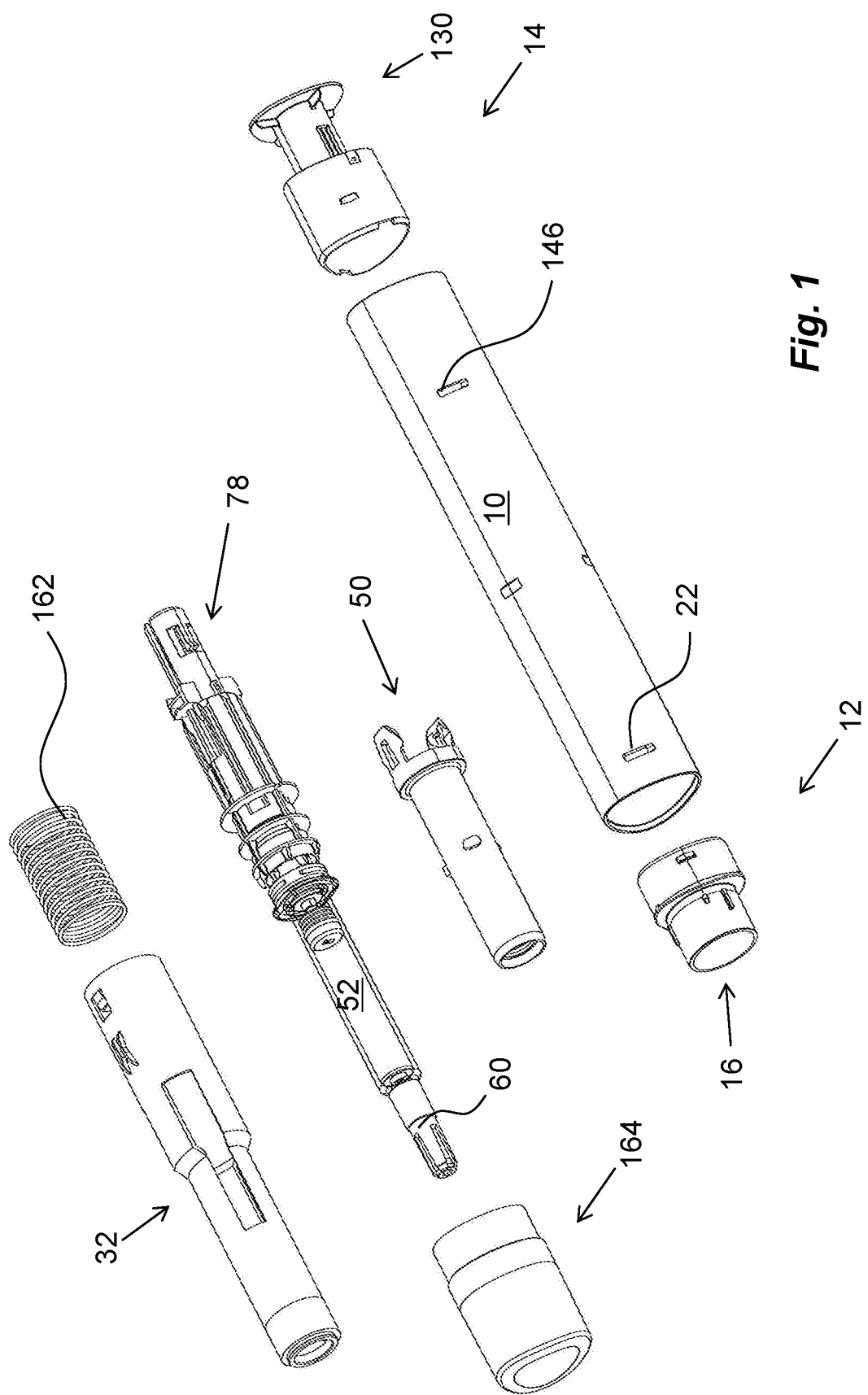

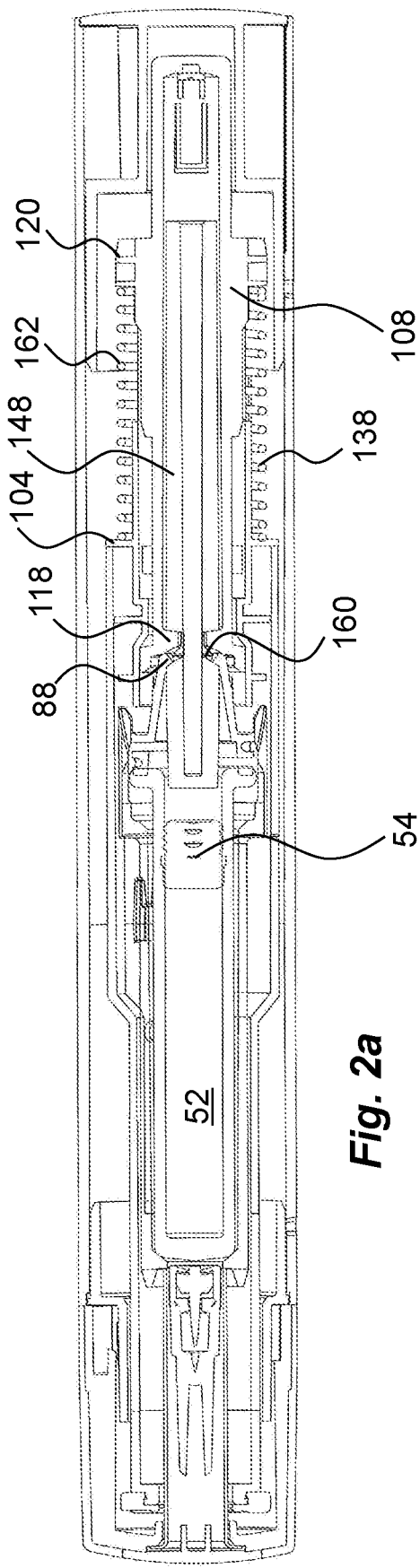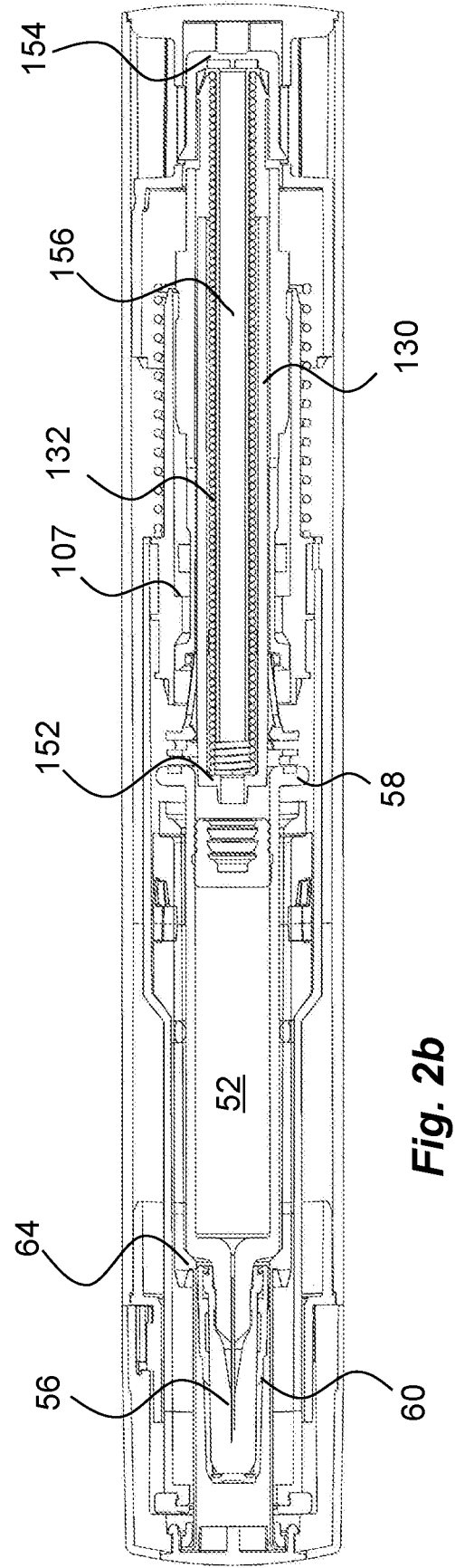
Fig. 2a
Fig. 2b

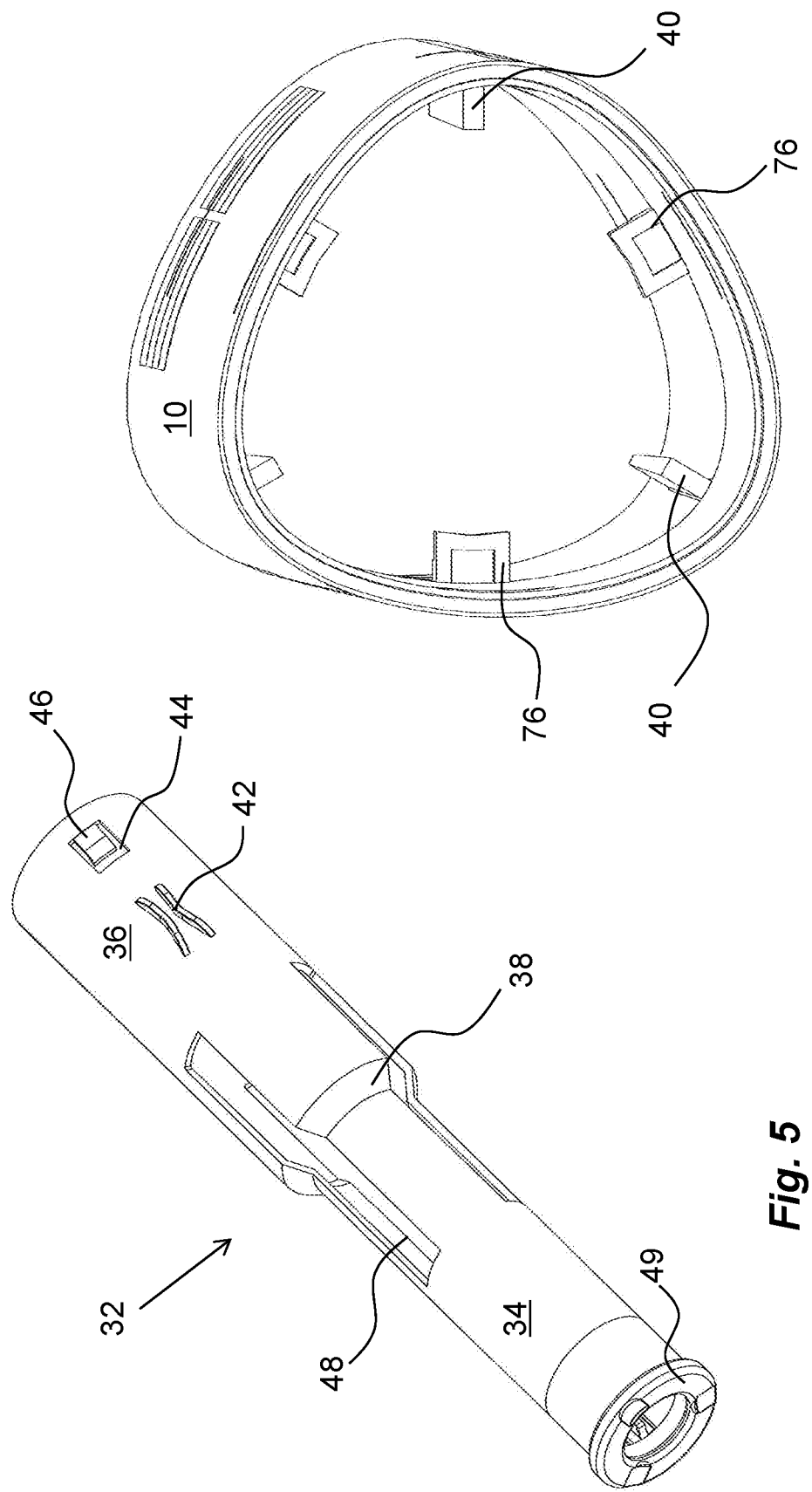

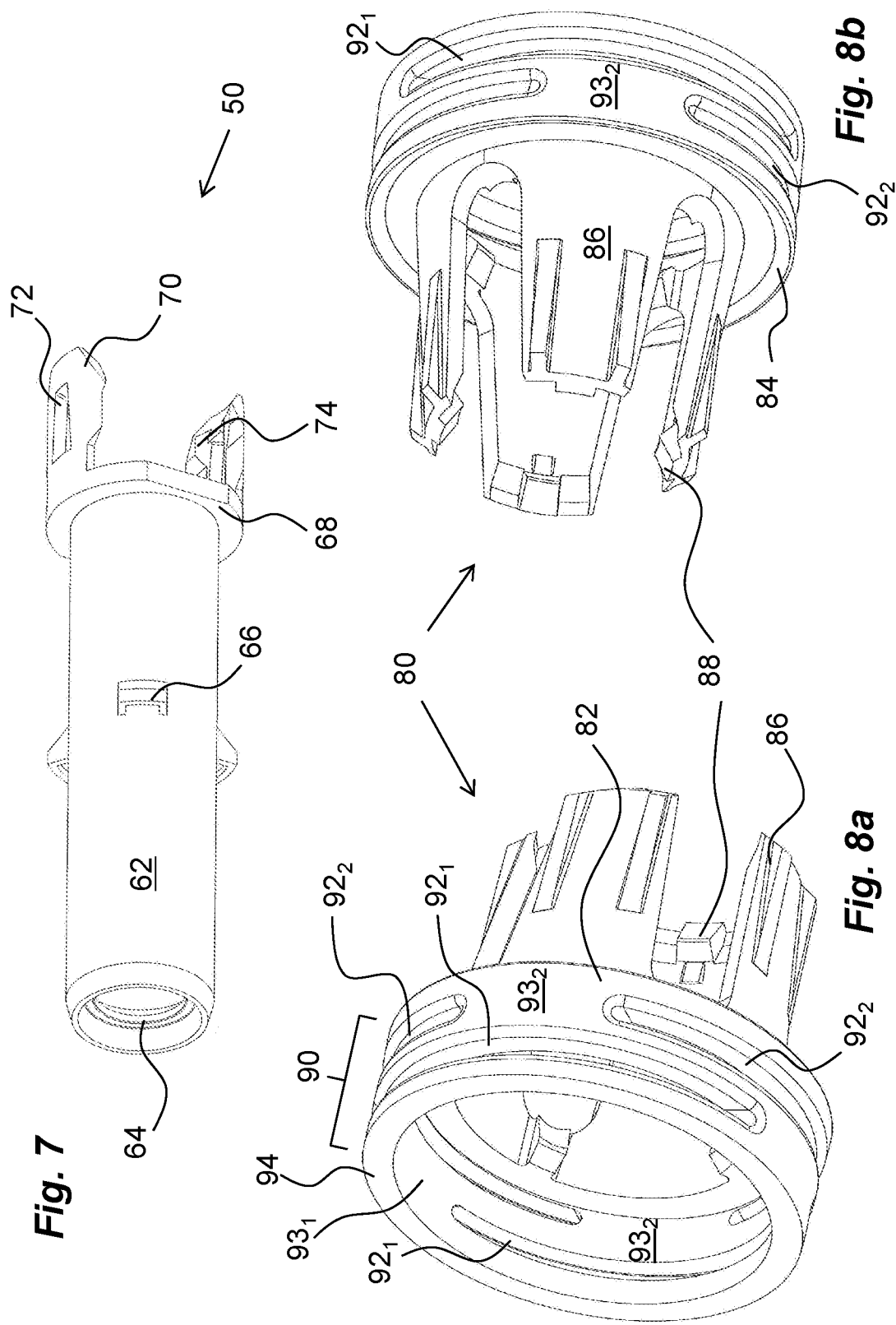

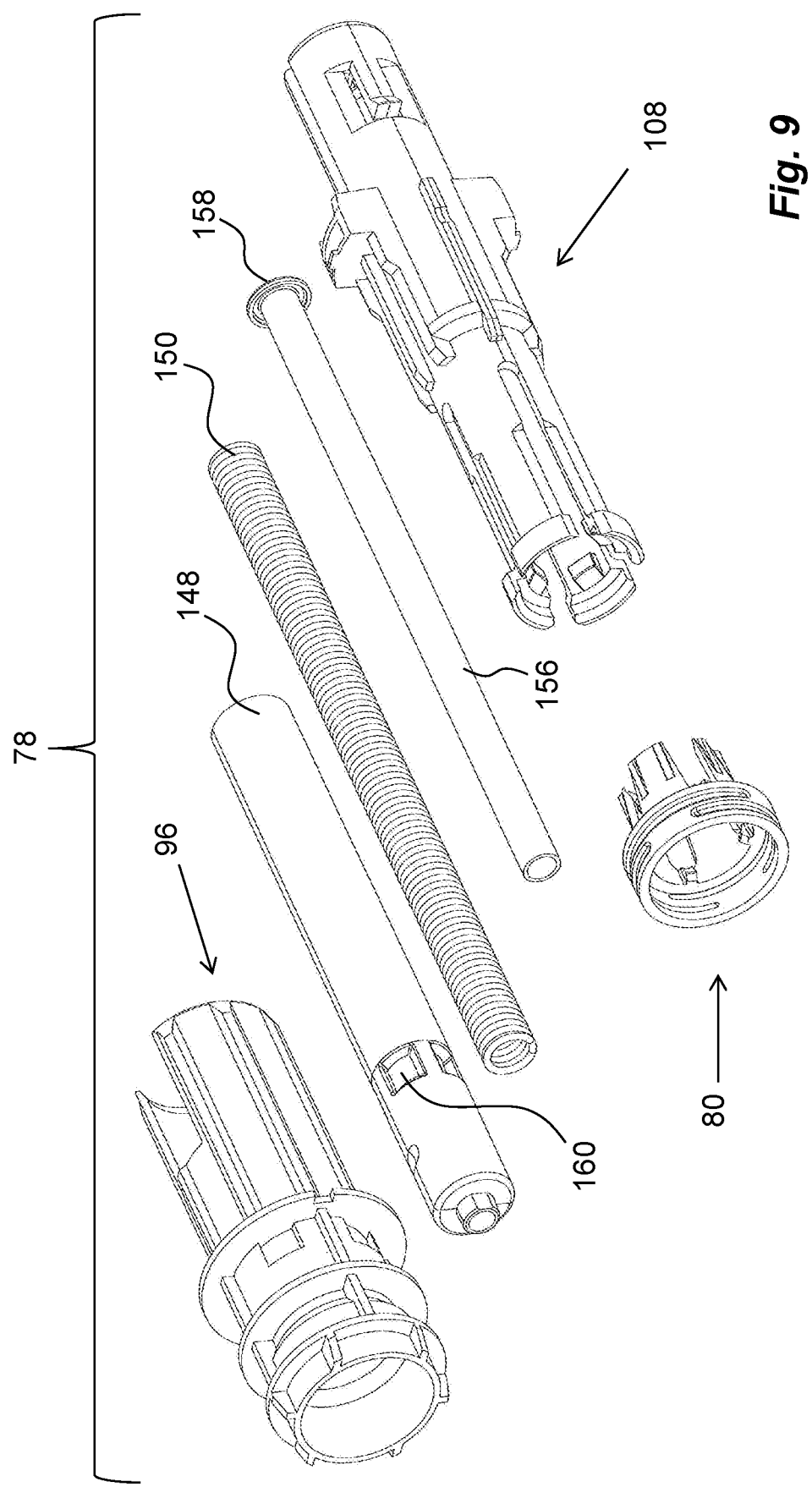

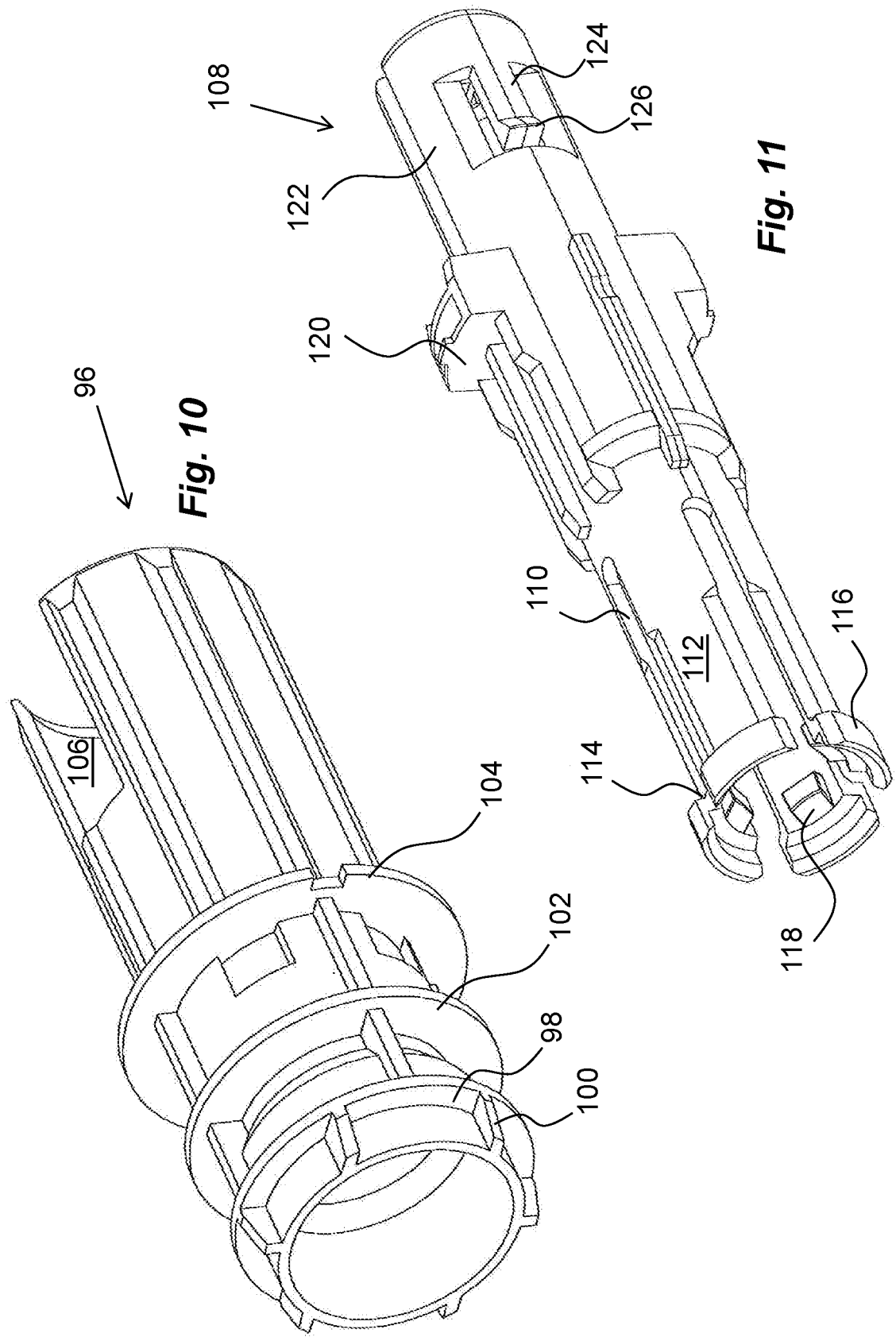

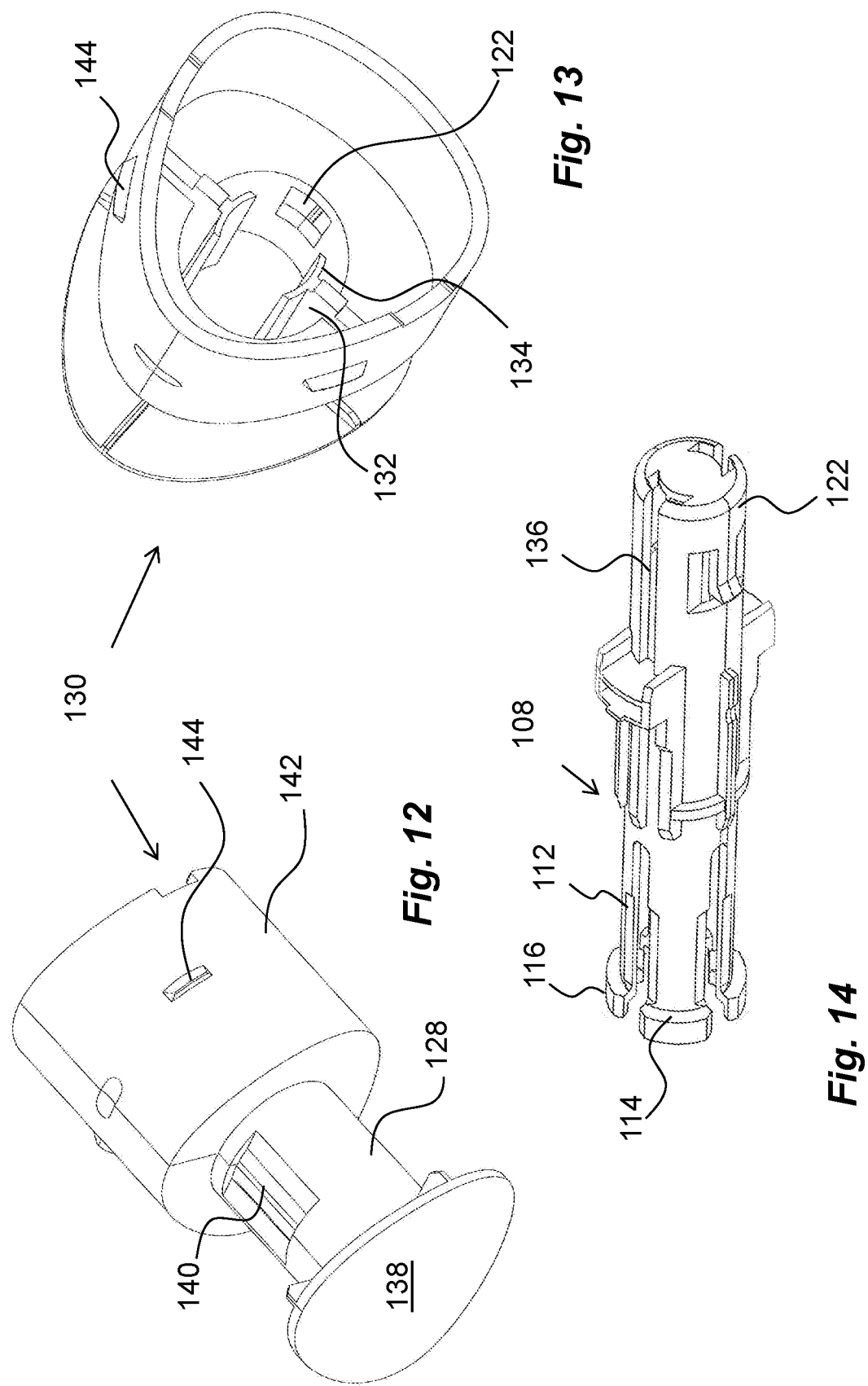

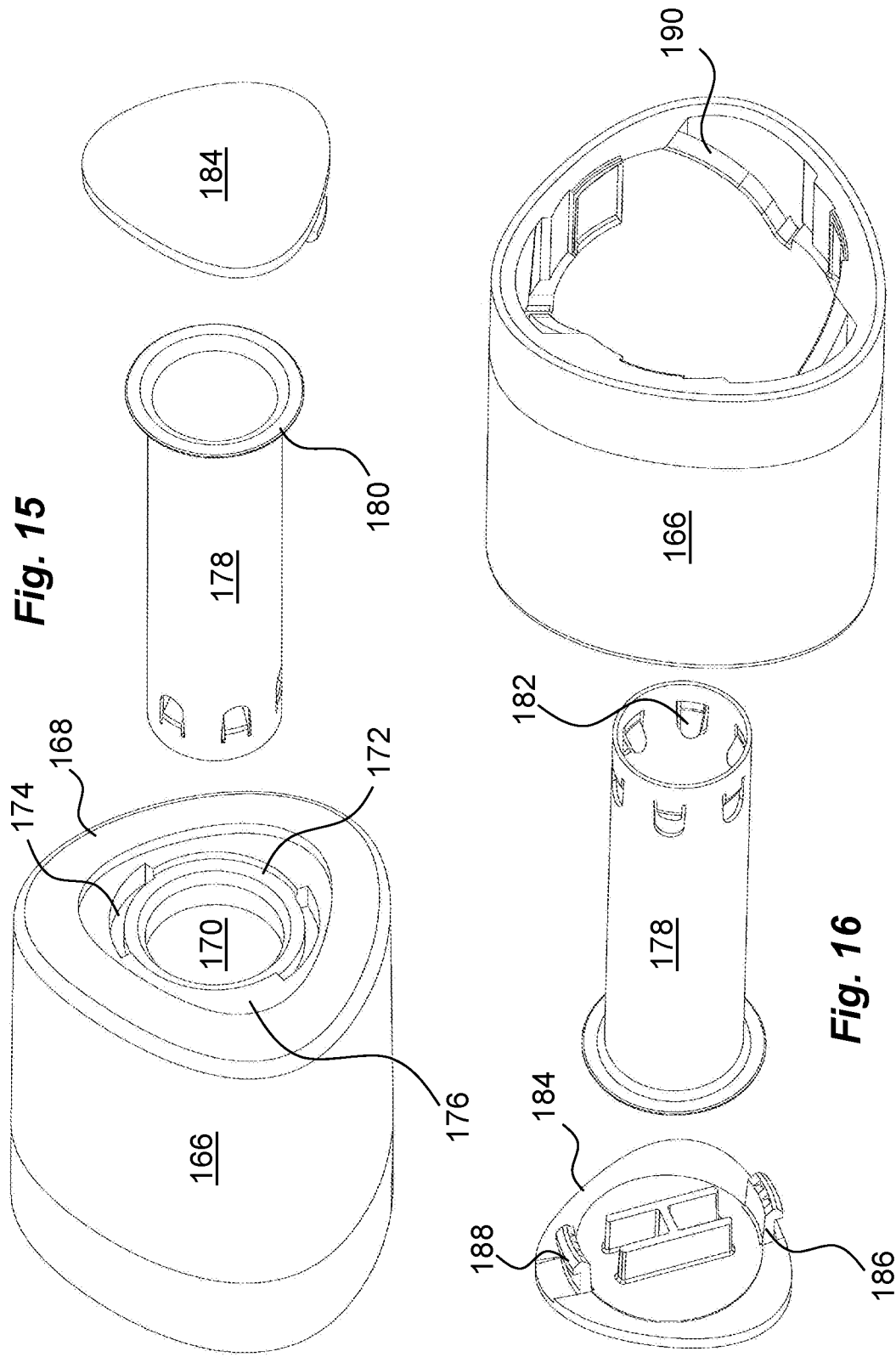

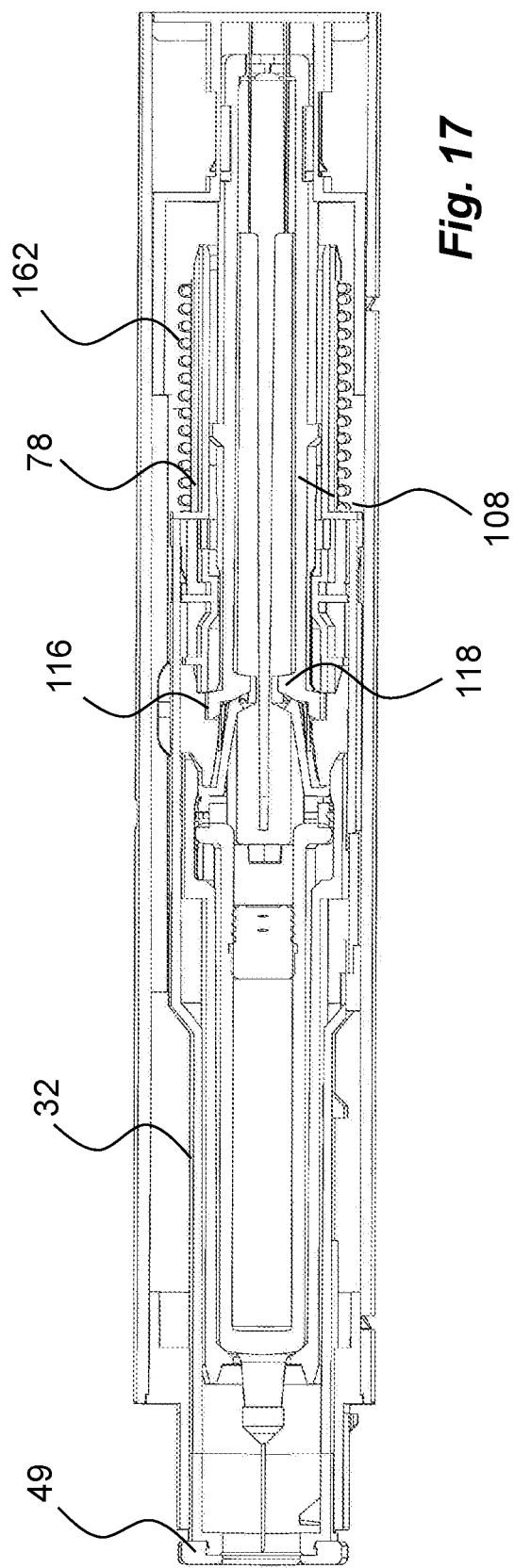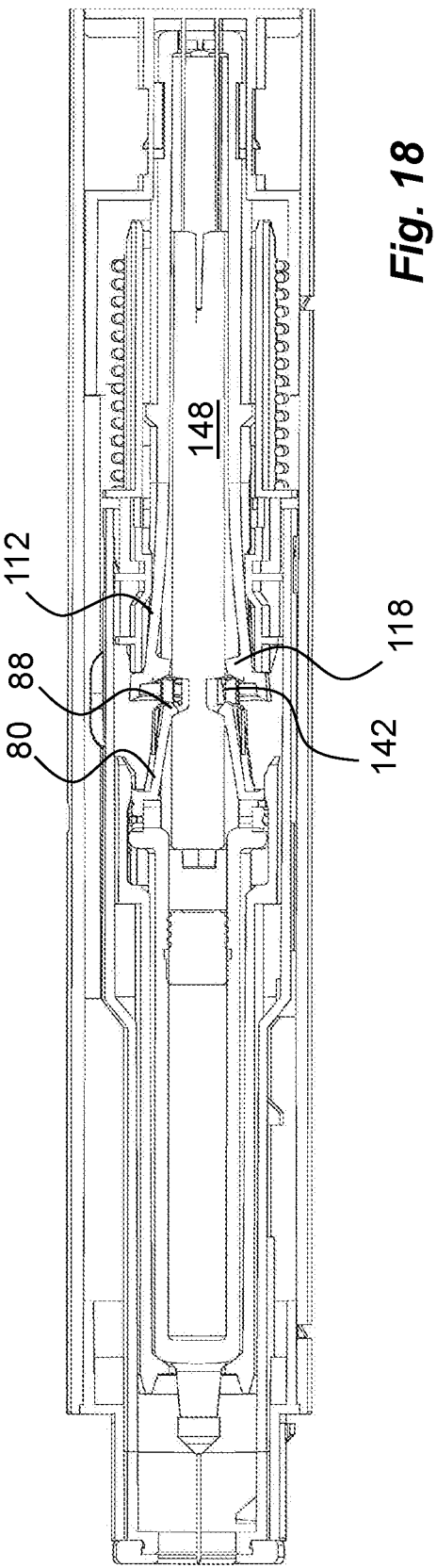

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/076821 filed Nov. 7, 2016, which claims priority to Swedish Patent Application No. 1551636-2 filed Dec. 14, 2015. The entire disclosure contents of these applications are herewith incorporated by reference into the present application.

TECHNICAL FIELD

The present disclosure relates to a medicament delivery device and in particular to an auto-injector which accommodates a movable medicament container.

BACKGROUND

There are a number of devices on the market that are capable of automatically or semi-automatically delivering doses of medicament, where these devices comprise a number of inter-acting components for obtaining the desired functions.

Some delivery devices are injectors capable of delivering doses of medicament by penetration of the user's skin and a subsequent injection of medicament. One such device is disclosed in the document EP 1349590, which comprises an activation mechanism in the form of a button placed at its distal end. The button may only activate the mechanism if the front end of the device is pressed against an injection site. When activated, the penetration mechanism inside the injector is released whereby a medicament container having a needle is forced forward by a spring such that the needle is pushed into the body of the user, followed by a delivery of medicament through the needle. When the injection is completed, the user withdraws the injector with the needle from the injection site, whereby a needle cover is pushed forward until it surrounds the needle and locks.

Normally, in order to protect the needle and ensure sterility of the needle, a needle shield such as a flexible needle shield (FNS) or a rigid needle shield (RNS) is arranged on the needle. Also, the delivery device comprises a front cap having a shield grabber. The front cap is removably attached to the front shell or housing. The medicament container, typically a glass medicament container, is normally not rigidly mounted within the housing due to tolerance variations between the parts. Especially a container made of glass often exhibits significant tolerance variations, thus creating a certain amount of play between the medicament container and the housing. If the medicament delivery device is accidentally dropped, or otherwise subjected to an impact, especially to a rear end thereof, the medicament container will move inside the medicament delivery device. The distance of movement will correspond to the amount of play between the housing and the medicament container. If the shield grabber is rigidly arranged in the cap, i.e. no play between the two parts, the movement of the medicament container could cause the needle shield to come loose from the needle since the needle is fixedly mounted to the medicament container and will follow the movements thereof, thus compromising the sterility of the needle.

SUMMARY

The aim of the present disclosure is to provide a medicament delivery device having a number of advantageous features. The aim is solved by a medicament delivery device provided with the features according to the independent patent claim. Preferable embodiments form the subject of the dependent patent claims.

According to a main aspect of the disclosure, it relates to a medicament delivery device comprising a medicament container having an attached medicament delivery member and a housing adapted to receive the medicament container. The medicament container is preferably movable between a retracted position in which the medicament delivery member is contained within the housing and an extended position in which the medicament delivery member extends from the housing in order to perform a penetration when the medicament delivery member is an injection needle.

Further, the medicament delivery device may comprise a drive unit that acts upon the medicament container to advance it from its retracted position to its extended position and expels its contents through the medicament delivery member. In that respect the medicament delivery device may further comprise a medicament container holder for carrying the medicament container as it is advanced wherein the medicament container holder has a proximal end through which the medicament delivery member extends and a distal end opposite to the proximal end.

The medicament delivery device may further be provided with a holding member releasably connected to the drive unit and attached to the medicament container holder and according to a favourable solution the holding member may comprise, at its proximal end, a biasing element arranged to bias the medicament container in the proximal direction in the medicament container holder and wherein the biasing element comprises a resilient structure in the form of a tubular wall provided with slots extending in the generally circumferential direction.

The advantage with the biasing element is on the one hand that the biasing element ascertains that the medicament container is provided with a biasing force that will minimize the risk of the medicament container being able to move inside the medicament container holder due to poor tolerances, where poor tolerances may result in gaps or play between the medicament container and the medicament container holder. Such play may in turn result in rattling noises when the medicament delivery device is handled, which often makes a negative impression on a user.

The play may also result in breakage of the medicament container if a force, e.g. a force from a drive unit of the medicament delivery device, is acting on the medicament container for expelling a dose of medicament. The force and the play may then cause an acceleration of the medicament container that may result a breakage when the accelerated medicament container hits a stationary element inside the medicament delivery device.

Another advantage is that there is a certain dampening action from the biasing element which may be important according to several aspects. For instance, should the medicament delivery device be accidentally dropped, the biasing element will only provide a limited movement of the medicament container inside the medicament container holder and at the same time a dampening action, which will remove the above-mentioned drawbacks of moving medicament containers, and may at the same time prevent breakage of the medicament container due to the impact when the medicament delivery device hits a hard surface.

The dampening action from the biasing element is also an advantage when the medicament container is exposed to forces during for example a dose delivery operation, reducing the risk of breakage of the medicament container.

Preferably the medicament container holder is arranged with a support surface at its proximal end, wherein the biasing element is arranged to bias the medicament container against the support surface. Since the medicament container holder is designed to accommodate the medicament container it is an advantage that the medicament container holder is arranged with a support surface for the medicament container against which support surface the biasing element may bias the medicament container.

According to one feasible solution, the tubular wall may be arranged with a first set of slots, where each slot in the set extends a part of the circumference of the tubular wall, forming a bridge between each successive slot. This solution provides a resiliency in the longitudinal direction of the medicament delivery device. In order to enhance the resiliency, a second set of slots may be provided, where each slot extend a part of the circumference of the tubular wall, forming a bridge between each successive slot, where the second set of slots is placed offset to the first set of slots as seen in a longitudinal direction. In order to even further enhance the resiliency, the bridges of the first set of slots may be placed offset in relation to the bridges of the second set of slots as seen in a circumferential direction.

Preferably, the biasing element may comprise a proximally directed end surface arranged to be in contact with a distally directed end surface of the medicament container. As an alternative, the biasing element is arranged integrated in the holding member and as another alternative the biasing element may be arranged as a separate component. Again, to further enhance the resiliency, the biasing element may be made of a resilient material.

According to a further solution, the holding element may be arranged with a number of distally directed arms, that the free ends of the arms are arranged with engagement elements that releasably engage corresponding engagement elements on a plunger rod of the drive unit. Thus, the movement of the plunger rod may then be transmitted to the holding element. According to a feasible solution, the engagement elements of the arms may comprise ledges and wherein the engagement elements of the plunger rod comprise recesses.

In order to releasably engage the holding element with the plunger rod, the drive unit may comprise a movable actuator sleeve arranged radially outside the arms of the holding element. Further, the drive unit may comprise an actuator arranged with holding elements arranged to releasably engage the holding elements of the plunger rod and the actuator may be operably connected to an activator for activating the drive unit. In this respect, according to a favourable solution, the activator may comprise a medicament delivery member guard extending from a proximal end of the medicament delivery device and movable from an initial position to an activation position. With this solution, the medicament delivery device may be activated by pressing the medicament delivery device against a dose delivery site, which provides a very straightforward and intuitive handling of the medicament delivery device.

These and other aspects of, and advantages with, the present disclosure will become apparent from the following detailed description of the disclosure and from the accompanying drawings.

BRIEF DESCRIPTION OF DRAWINGS

In the following detailed description of the present disclosure, reference will be made to the accompanying drawings, of which FIG. 1 is an exploded view of a medicament delivery device according to the present application, FIG. 2 is a cross-sectional view of the medicament delivery device of FIG. 1, FIGS. 3-16 are detailed views of components comprised in the medicament delivery device of FIG. 1, and FIGS. 17-22 are cross-sectional views of the medicament delivery device of FIG. 1 in different functional stages.

DETAILED DESCRIPTION

In the present application, the term "distal part/end" refers to the part/end of the device, or the parts/ends of the members thereof, which under use of the device, is located the furthest away from a delivery site of a user. Correspondingly, the term "proximal part/end" refers to the part/end of the device, or the parts/ends of the members thereof, which under use of the device is located closest to the delivery site of the user.

Figure 4:
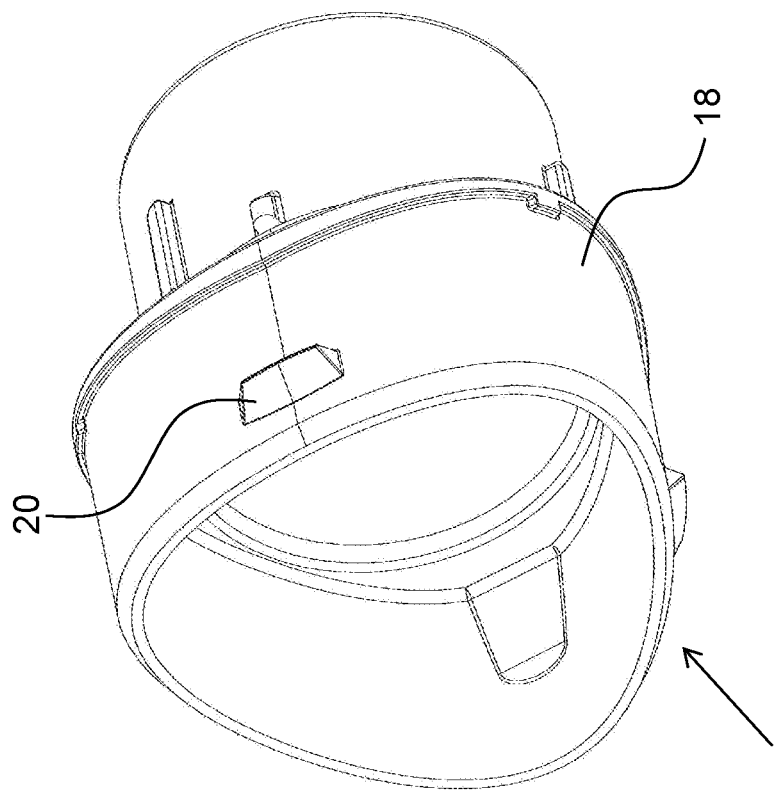
Figure 3:
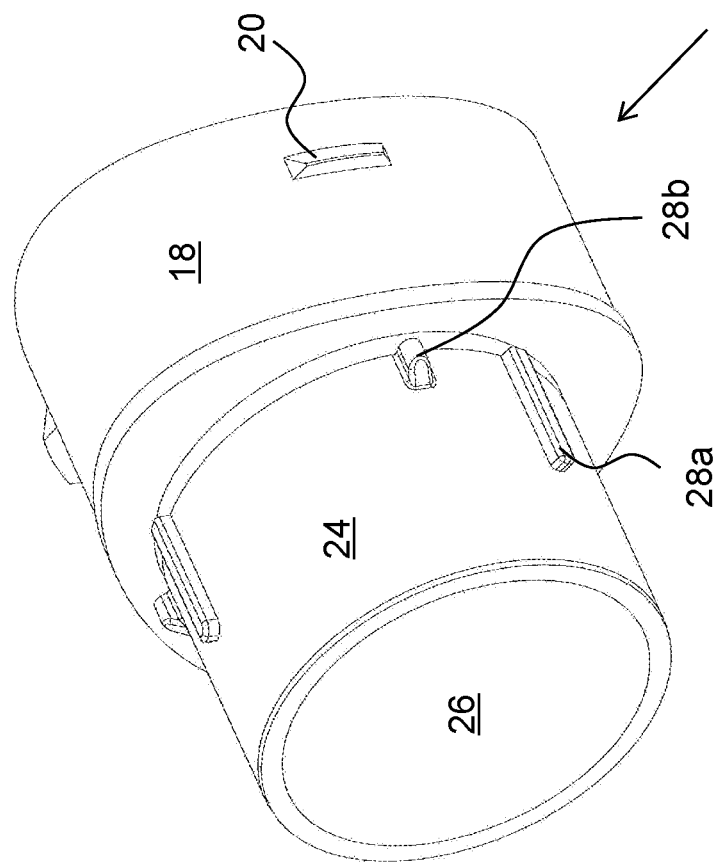

The medicament delivery device shown in the drawings comprises a generally elongated tubular housing 10 having opposite proximal end 12 and distal end 14. At the proximal end of the housing 10 an end piece 16, hereafter named front end cover, is arranged to be attached. The front end cover 16, FIGS. 3 and 4, comprises a generally tubular body 18 having a shape so as to fit into the proximal end of the housing 10 and to be attached to the housing 10 with outwardly directed protrusions 20 on the outer surface of the body 18 fitting into recesses 22 of the housing 10, FIG. 1. The front end cover 16 is further arranged with a generally tubular proximal end part 24, provided with a central passage 26. The outer surface is further arranged with a number of ledges, 28a, 28b, the function of which will be described below.

A medicament delivery member guard 32, FIGS. 1 and 5, is arranged to move longitudinally in relation to the housing 10 and to protrude through the central passage 26 of the front end cover 16. The medicament delivery member guard 32 comprises a generally elongated tubular first section 34 having a diameter somewhat smaller than the inner diameter of the central passage 26 so as to provide support of the medicament delivery member guard 32 in the radial direction. The first section 34 is attached to a second section 36 having a slightly larger diameter via an inclined transition section 38. The medicament delivery member guard 32 is further supported inside the housing by longitudinally extending ledges 40 on its inner surface; FIG. 6. One of these ledges 40 is arranged to fit between two ledge sections 42 on an outer surface of the second section 36 of the medicament delivery member guard 32, providing a rotational lock of the medicament delivery member guard 32 in relation to the housing 10. At the distal end of the medicament delivery member guard 32 two openings 44 are arranged opposite each other, where each opening 44 is arranged with a somewhat inwardly projecting, flexible, tongue 46, FIG. 5. The medicament delivery member guard 32 is further arranged with three elongated slits 48 along a part of its extension. At the proximal end of the medicament delivery member guard 32, a generally ring-shaped extension element 49 is arranged, preferably snap-fitted to the proximal end of the medicament delivery member guard 32. The extension element 49 is intended to function as a contact member against a dose delivery site as will be described.

The device also comprises a medicament container holder mechanism comprising a medicament container holder 50, FIGS. 1 and 7, slidably and coaxially arranged within the medicament delivery member guard 32. The medicament container holder 50 is arranged to accommodate a generally tubular elongated medicament container 52 provided with a movable stopper 54 inside, FIG. 2*a*, a medicament delivery member 56 at a proximal end of the medicament container 52 and an outwardly directed flange 58, FIG. 2*b*, at a distal end of the medicament container 52. The medicament delivery member 56 is protected by a medicament delivery member shield 60, FIG. 2*b*, that in the embodiment shown is a rigid needle shield or RNS. It is however to be understood that other types of medicament delivery member shields such as flexible needle shields or FNS's may be used.

The medicament container holder 50 has the form of a generally tubular body 62 and the proximal part of the medicament container holder 50 is arranged with an annular support ledge 64, FIGS. 2*b* and 7, which support ledge 64 provides support and fixation surfaces for a proximal part of the medicament container 52. The medicament container holder 50 is further arranged with three outwardly directed protrusions 66 that are arranged to fit into the slits 48 of the medicament delivery member guard 32. The protrusions 66 are arranged to act as guide members between the medicament delivery member guard 32 and the medicament container holder 50, the function of which will be described below.

The distal end of the medicament container holder 50 is arranged with an annular, proximally directed, ledge 68. On the ledge 68, two distally extending tongues 70 are attached, where each tongue 70 is arranged with an opening 72 and two inwardly directed ledges 74 on the distal edge of each opening, FIG. 2. The ledge 68 is further arranged to cooperate with inwardly directed stop ledges 76 arranged on the inner surface of the housing 10, FIG. 6, as will be described below.

The medicament delivery device according to the figures further comprises a drive unit 78, FIG. 9. It comprises a holding member 80, FIGS. 8-10, which comprises a tubular wall 82 having a distally directed annular ledge 84 arranged around its circumference and a number of flexible tongues 86 directed towards the distal end of the device and wherein each tongue 86 is arranged with first engagement elements that in the embodiment shown are radial inwardly directed ledges 88. Further, according to one aspect of the disclosure, the tubular wall 82 of the holding member 80 is arranged with a biasing element 90 that comprises a number of sets of slots 92, FIG. 8, such as a first set of slots 92$_1$ where each slot 92$_1$ in the first set extends a part of the circumference of the tubular wall 82, forming a bridge 93$_1$ between each successive slot. The biasing element 90 may further be arranged with a second set of slots 92$_2$ placed in the same manner as the first set whereby bridges 93$_2$ are formed between each successive slot 92$_2$ of the second set. The sets of slots 92$_1$, 92$_2$, are preferably placed offset to each other in the circumferential direction such that the bridges 93$_1$ of one set are placed next to a slot 92$_2$ of a second set as seen in the longitudinal direction, as seen in FIG. 8, whereby a resilient action is obtained in the longitudinal direction of the medicament delivery device. A proximal end surface 94, FIG. 8*a*, is intended to be in contact with a distal surface of the flange 58 of the medicament container 52.

The device also comprises an actuator sleeve 96, FIG. 10, which is slidably and coaxially arranged within the housing 10. The actuator sleeve 96 has a tubular shape and comprises a first annular ring 98 at its proximal end. A number of bevelled ledges 100 are arranged extending from the proximal edge of the actuator sleeve 96 to the first annular ring 98. A second annular ring 102 and a third annular ring 104 are arranged along the length of the actuator sleeve 96. At the distal end of the actuator sleeve two cut-outs 106 are arranged, positioned on opposite sides along the circumference. Further, the actuator sleeve 96 is arranged with a distally directed annular ledge 107, FIG. 2*b*, the function of which will be described below.

The actuator sleeve 96 is intended to be connected to the medicament delivery member guard 32 in that the distal end of the medicament delivery member guard 32 is pushed onto the proximal end of the actuator sleeve 96, which is facilitated by the bevelled ledges 100, until a distal edge of the medicament delivery member guard 32 abuts a proximal surface of the second annular ring 102, whereby the flexible tongues 46 will be positioned with their free ends in contact with a distally directed surface of the first annular ring 98.

The device further comprises an actuator 108 which is slidaby and coaxially arranged within the actuator sleeve 96 and which has a mainly tubular shape. A number of longitudinally directed cut-outs 110 are arranged along the proximal end of the actuator 108 so as to form flexible tongues 112, FIG. 11. The proximal end of each flexible tongue 112 has an inclined transition surface 114 which meets with a band-shaped part 116 with enlarged diameter. On the inner surface adjacent the transition surface, third engagement elements are provided that in the embodiment shown are inwardly directed protrusions 118 that are arranged on each tongue 112. Further, the actuator 108 is arranged with radially outwardly extending stop ledges 120 that are arranged to fit into the cut-outs 106 on the actuator sleeve 96. The actuator 108 is also arranged with a distally directed tubular guide element 122, which is arranged with two proximally directed arms 124 that are flexible in the generally radial direction. The free ends of the arms 124 are arranged with outwardly directed, wedge-shaped, protrusions 126.

The guide element 122 is arranged to fit into a generally tubular guide post 128 that is comprised in a rear end cover 130, FIGS. 12 and 13. The interior of the guide post 128 is arranged with longitudinally extending ledges 132, wherein the inwardly edges of the ledges 132 are arranged with somewhat curved flanges 134. The ledges 132 and the flanges 134 are designed to fit into longitudinally extending grooves 136, FIG. 14, in the guide element 122, which grooves 136 have corresponding shape to the shape of the ledge/flange 132/134 as seen in a cross-sectional view. A distal end of the guide post 128 is attached to, or made integral with, an end wall 138, which closes the distal end of the medicament delivery device when the rear end cover 130 is attached to the housing 10. Further, the protrusions 126 of the arms 124 are arranged to fit into longitudinally extending slits 140 in the guide post 128. The proximal end of the guide post 128 is further attached to, or made integral with, a generally tubular locking element 142, which locking element 142 has an outer shape as to fit into the housing 10. Further the locking element 142 is arranged with outwardly directed protrusions 144 that are arranged to fit into recesses 146 in the housing 10, FIG. 1.

The drive unit 78 further comprises a plunger rod 148, FIG. 9, arranged to act on the stopper 50 inside the medicament container 52. A drive spring 150 is arranged inside the plunger rod 148 between a proximal end wall 152 of the plunger rod 148 and a distal end wall 154 of the actuator 108, FIG. 2*b*. A guide rod 156 is arranged inside the drive spring 150, provided with an end plate 158 at its distal end, which end plate 158 is abutting the distal end wall 154 of the actuator 108.

The plunger rod 148 is arranged with second engagement elements that in the embodiment shown are a number of recesses 160, FIG. 9, where each recess 160 has a mutual shape as that of the protrusions 118 of the actuator 108 and as that of the ledges 88 of the holding member 80 so that the inwardly directed protrusions 118 of the actuator 108 and the radial inwardly directed ledges 88 of the holding member 80 fit into and engage the recesses 160, FIG. 2a.

The device further comprises a medicament delivery member guard spring 162 which has a proximal end resting on a distally directed surface of the third annular ring 104 of the actuator sleeve 96 and a distal end resting on a proximal surface of the stop ledges 120 of the actuator 108, FIG. 2a.

Also, the medicament delivery device comprises a medicament delivery member shield remover 164, FIGS. 1, 15 and 16. It comprises a generally tubular grip part 166 provided with an end wall 168, which end wall 168 is arranged with a central passage 170. Around the central passage 170 an annular groove 172 is arranged. Further, two arc-shaped slits 174 are arranged radially outside the annular groove 172. The central passage 170 and the arc-shaped slits 174 are placed in a recess 176 in the end wall 168. A medicament delivery member shield grabber 178 is further provided. It comprises a generally tubular member provided with a diameter generally corresponding to the diameter of the central passage and having an outwardly extending annular flange 180 at a proximal end arranged to fit into the annular groove 172. The distal end of the medicament delivery member shield grabber 178 is arranged with proximally directed tongues 182 that are somewhat inclined inwards, the function of which will be described below. The medicament delivery member shield remover 164 is further arranged with a generally plate-shaped lid 184 that is designed to fit into the recess 176 of the end wall 168. The lid 184 is arranged with distally directed arms 186, wherein the free ends of the arms 186 are arranged with outwardly directed wedge-shaped ledges 188, arranged to cooperate with the arc-shaped slits 174 of the end wall 168.

When the medicament delivery member shield remover is assembled, the medicament delivery member shield grabber 178 is entered through the central passage 170 from the distal end, wherein the annular flange 180 is placed in the annular groove 172. The lid 184 is then pushed with its arms 186 through the arc-shaped slits 174 and is placed in the recess 176, whereby the wedge-shaped ledges 188 of the arms 186 will engage with the end wall 168 to attach the lid 184 to the grip part 166. This also locks the position of the medicament delivery member shield grabber 178 in the medicament delivery member shield remover 164. The medicament delivery member guard grabber 178 is now locked in the longitudinal direction but may rotate in relation to the grip part 166. The medicament delivery member shield remover 164 is further arranged with distally directed cam-shaped ledges 190, FIG. 16, on an inner part of the grip part 166. These cam-shaped ledges 190 are intended to interact with the ledges 28a, 28b of the front end cover 16 as will be described.

The medicament delivery device is intended to function as follows. When the device is assembled, and in a non-activation position, the plunger rod 148 is held against the force of the pre-tensioned drive spring 150 by the third engagement elements, i.e. the inwardly directed protrusions 118 of the tongues 112 of the actuator 108 situated in, and engaging, the second engagement elements, i.e. the recesses 160 of the plunger rod 148, and by the actuator sleeve 96 which surrounds and prevents the tongues 112 from moving radially outwards. Further, the first engagement elements, i.e. the ledges 88 of the holding member 80 are also arranged in the recesses 160, FIG. 2a. The inwardly directed ledges 74 on the tongues 70 of the medicament container holder 50 pass the distal end surface of the annular ledge 84 of the holding member 80 for connecting the medicament container holder 50 to the holding member 80, and at the same time the tongues 46 at the distal end of the medicament delivery member guard 32 fit the distal surface of the first annular ring 98 of the actuator sleeve 96 for connecting the medicament delivery member guard 32 to the actuator sleeve 96.

In order to get the medicament delivery device ready for use, the medicament delivery member shield remover 164 is removed from the proximal end by turning the medicament delivery member shield remover 164 in relation to the housing 10 and the front end cover 16 whereby the ledges 28a and 28b will ride on the cam-shaped ledges 190, which causes the medicament delivery member shield remover 164 to be moved in the proximal direction in relation to the front end cover 16. The medicament delivery member shield grabber 178 will also be moved in the proximal direction but will not rotate because of the attachment by the annular flange 180 fitting into the annular groove 172 and held in place by the lid 184, allowing the medicament delivery member shield grabber 178 to be stationary when the medicament delivery member shield remover 164 is turned. When the medicament delivery member shield grabber 178 is moved in the proximal direction, the inwardly directed tongues 182 will engage the outer surface of the medicament delivery member shield 60 and pull it along with the medicament delivery member shield remover 164, whereby the medicament delivery member 56 will be exposed. The medicament delivery device may now be placed with its proximal end against a dose delivery site.

The medicament delivery member guard 32, and the actuator sleeve 96 connected to the medicament delivery member guard 32, are arranged to be moved coaxially and distally in relation to the housing 10 and to the actuator 108 against the force of the medicament delivery member guard spring 162, when the proximal part of the medicament delivery member guard 32 with its extension element 49 is pressed against the injection site, FIG. 17. When the actuator sleeve 96 moves distally, the band-shaped part 116 of the actuator 108 protrudes out of the proximal end of the actuator sleeve 96, FIG. 17, and the resilient properties of the tongues 112 of the actuator 108 allows the proximal end of the tongues 112 to flex radially outwards, causing the inwardly directed protrusions 118 of the actuator 108 to be released from the recesses 160 of the plunger rod 148, FIG. 18. However, the ledges 88 of the holding member 80 are still in the recesses 160 of the plunger rod 148 and with the proximal end surface 94 against the distal surface of the flange 58 of the medicament container 52, whereby the force from the drive spring 150 urges the plunger rod 148 and thereby the holding member 80 in the proximal direction.

Figure 19:
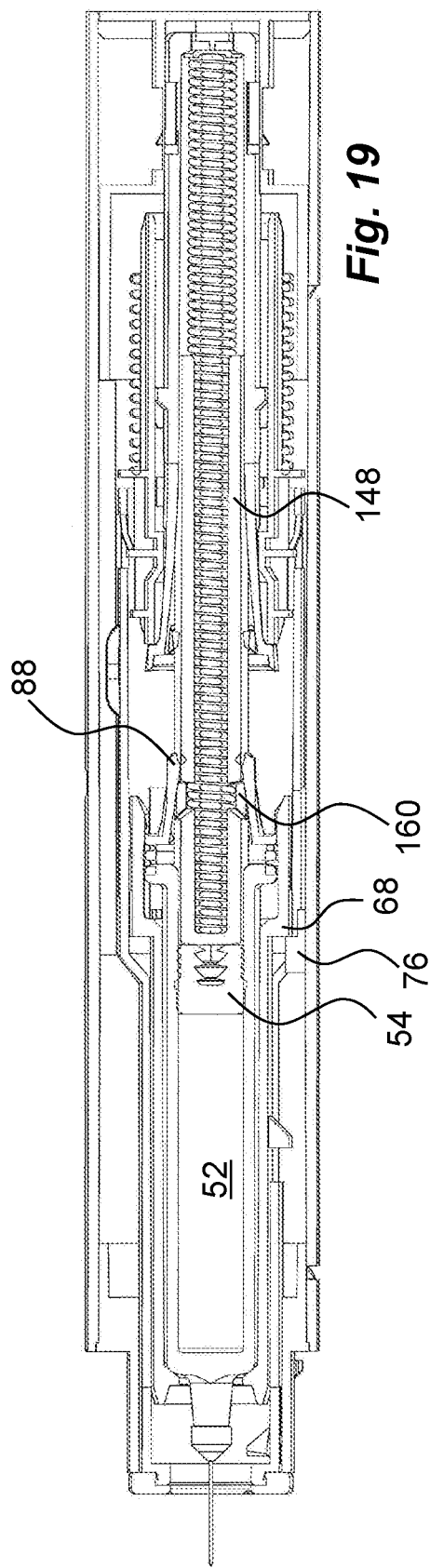

Since the holding member 80 is attached to the medicament container holder 50, the medicament container holder 50 with the medicament container 52 will also move in the proximal direction, whereby a penetration of the injection needle 52 into the dose delivery site is performed, FIG. 19. In this respect, the biasing element 90, acting on the flange 58 of the 13 medicament container 52 ascertains that there is a firm contact between the medicament container 52 and the support surface 64 of the medicament container holder 50 when the force from the drive spring 150 acts on the holding member 80, thereby reducing the risk of breaking the medicament container 52 which otherwise could occur if there was a gap between the medicament container 52 and the support surface 64 when the force from the drive spring 150 was applied to the distal end of the medicament container 52 via the holding member 80.

The biasing element 90 has further advantages in that the force from the holding member 80 on the flange 58 at the distal end of the medicament container 52 is dampened and is thus not so immediate and forceful due to the biasing element 90 and its resilient properties. The resilient properties are on the one hand due to the slots 92 that are placed offset both in the circumferential direction and the longitudinal direction and on the other hand dependent on the choice of material of the holding member 80 or of the biasing element 90. The latter may be especially important if the biasing element 90 is provided as a separate component that may be attached to the holding member 80. The important feature is however that the biasing element 90 is capable of reducing or minimizing any gaps between the medicament container 52 and the medicament container holder 50 as well as handling the forces from the drive spring 150 so as to avoid breakage of the medicament container 52 and also to provide a smooth start of the penetration sequence.

When the medicament container holder 50 has reached its most proximal position, which constitutes the penetration depth, it is forced to a stop in that the proximally directed ledge 68 of the medicament container holder 50 abuts distally directed surfaces of the stop ledges 76 on the inner surface of the housing 10, FIG. 19. However the force of the drive spring 150 acting on the plunger rod 148 is so high that the ledges 88 of the holding member 80 are forced out of the protrusions 160 of the plunger rod 148.

Figure 20:
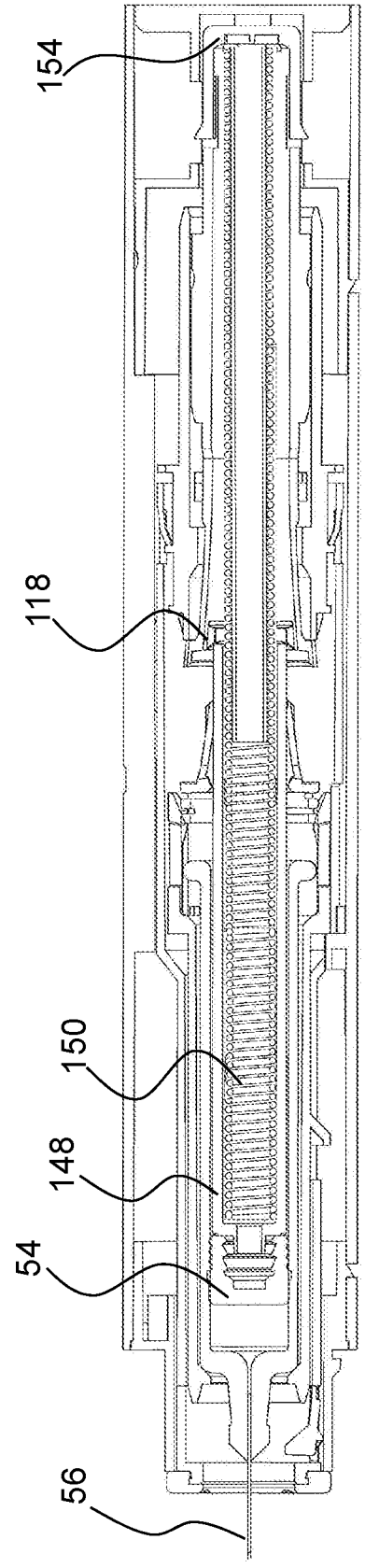
Figure 21:
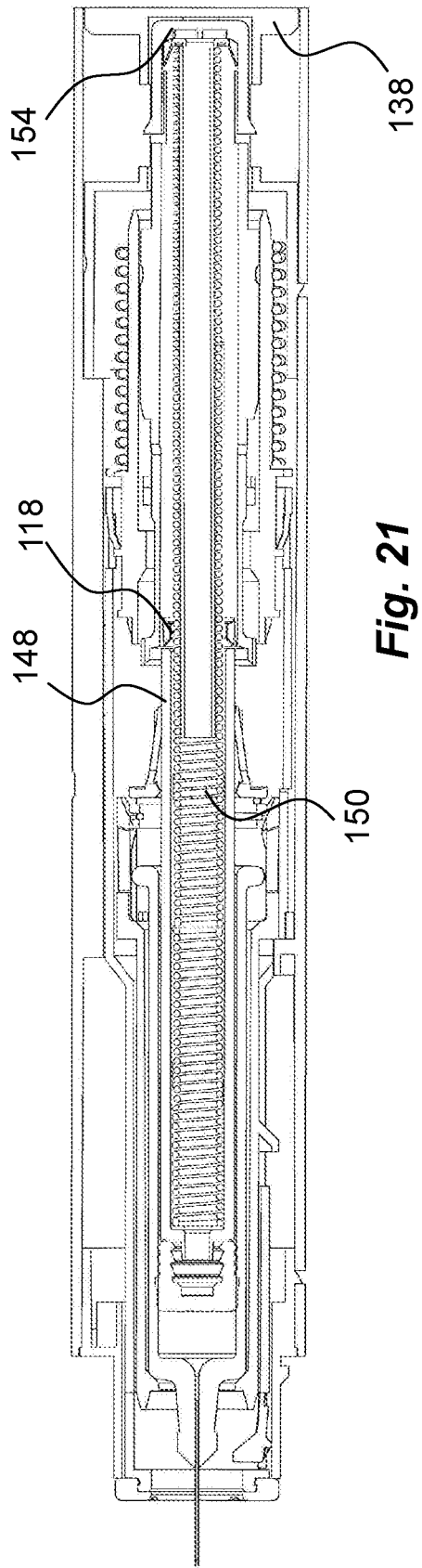

The force from the drive spring 150 continues to urge the plunger rod 148 to move the stopper 54 inside the medicament container 52 and the liquid medicament is administered to the user via the medicament delivery member 56 until the stopper 54 reaches the inner proximal end of the medicament container 52, FIG. 20. After the liquid medicament has been injected and the distal end of the plunger rod 148 has passed the inwardly directed protrusions 118 of the actuator 108, the tongues 112 are radially moved inwards, FIG. 21. Because the drive spring 150 is also acting on the inner surface of the distal end wall 154 of the actuator 108 and has a remaining force, the actuator 108 is moved distally until the distally directed surface of the distal end wall 154 of the actuator 108 strikes against a proximally directed surface of the end wall 138 of the rear end cover 130 giving an audible signal to the user indicating that the delivery e.g. the injection has been completed and that the device can be safely removed from the dose delivery site.

Figure 22:
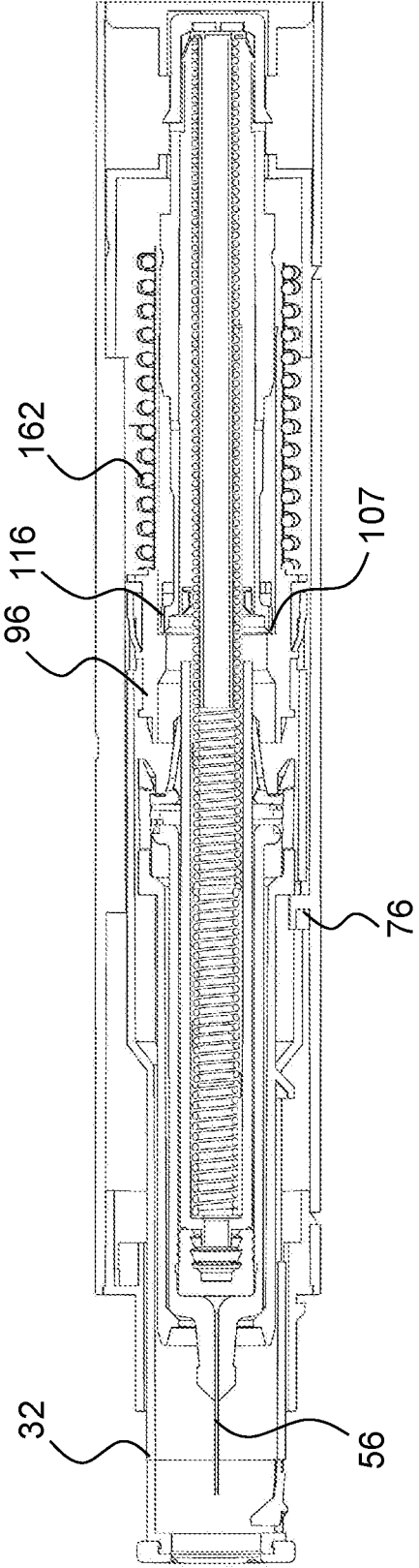

When the medicament delivery device is removed from the dose delivery site the medicament delivery member guard 32 is urged in the proximal direction by the medicament delivery member guard spring 162 via the actuator sleeve 96, FIG. 22, thereby covering the medicament delivery member 56. The medicament delivery member guard 32 is stopped in the proximal direction when proximally directed end surfaces of the slits 48 hit the stop ledges 76 on the inner surface of the housing 10. Further, the actuator sleeve 96 has now moved in the proximal direction in relation to the actuator 108 such that the band-shaped part 116 of the actuator 108 passes the distally directed annular ledge 107 of the actuator sleeve 96, FIG. 22, whereby the tongues 112 flex radially outwards and a proximal end surface of the band-shaped part 116 is moved in contact with the distally directed annular ledge 107, thereby locking the actuator sleeve 96 and thereby the medicament delivery member guard 32 from being moved in the distal direction. The medicament delivery member 56 is thus safely covered by the medicament delivery member guard 32. The medicament delivery device can now be discarded.

It is to be understood that the embodiment described above and shown in the drawings is to be regarded only as a non-limiting example of the present disclosure band that it may be modified in many ways within the scope of the patent claims.

The invention claimed is:

1. A medicament delivery device comprising:
   a medicament container comprising a syringe barrel having an attached medicament delivery member and a radially extending flange having a distal end surface;
   a housing having a longitudinal axis and adapted to receive the medicament container, the medicament container being movable between a retracted position in which the medicament delivery member is contained within the housing and an extended position in which the medicament delivery member extends from the housing;
   a rear end cover axially fixed relative to the longitudinal axis of the housing and fixedly attached to an open distal end of the housing, where the rear end cover has an internal portion comprising a radially inward extending flange;
   an actuator having distal end and comprising a longitudinal groove that is in sliding engagement with the radially inward extending flange such that actuator is rotationally fixed relative to the housing;
   a drive unit that acts upon the medicament container to advance it from its retracted position to its extended position and to expel its contents through the medicament delivery member; and
   a medicament container holder for carrying the medicament container as it is advanced, the medicament container holder having a proximal end that comprises a support surface and is configured with a through hole through which the medicament delivery member extends and a distal end opposite the proximal end; and
   a holding member releasably connected to the drive unit and attached to the medicament container holder, where the drive unit exerts a biasing force that moves the holding member proximally when the holding member is attached to the drive unit,
   wherein the holding member comprises, at its proximal end, a biasing element having a proximal end surface that engages with and biases the distal end surface of the radially extending flange, where the drive unit biases the biasing element proximally so as to bias the medicament container in a proximal direction within the medicament container holder such that the medicament container abuts the support surface so that the medicament container and the medicament container holder are axially fixed relative to each other,
   wherein during medicament delivery member penetration the biasing element dampens the biasing force of the drive unit exerted upon the distal end surface of the medicament container to prevent breakage of the medicament container, and
   wherein the biasing element comprises a resilient structure in the form of a tubular wall provided with slots extending in the generally circumferential direction.

2. The medicament delivery device according to claim 1, wherein the tubular wall is arranged with a first set of slots, where each slot extends a part of the circumference of the tubular wall, forming a bridge between each successive slot.

3. The medicament delivery device according to claim 2, wherein the tubular wall further is provided with second set of slots that each extend a part of the circumference of the tubular wall, forming a bridge between each successive slot, where the second set of slots is placed offset to the first set of slots as seen in a longitudinal direction.

4. The medicament delivery device according to claim 3, wherein the bridges of the first set of slots are placed offset in relation to the bridges of the second set of slots as seen in a circumferential direction.

5. The medicament delivery device according to claim 1, wherein said biasing element is arranged integrated in said holding member.

6. The medicament delivery device according to claim 1, wherein said biasing element is arranged as a separate component.

7. The medicament delivery device according to claim 1, wherein said biasing element is made of a resilient material.

8. The medicament delivery device according to claim 1, wherein said holding element is arranged with a number of distally directed arms having free ends that are arranged with first engagement elements that releasably engage corresponding second engagement elements of a plunger rod of said drive unit.

9. The medicament delivery device according to claim 8, wherein said first engagement elements comprise ledges and wherein said second engagement elements comprise recesses.

10. The medicament delivery device according to claim 8, wherein said drive unit comprises a movable actuator sleeve arranged radially outside said arms of said holding element, for releasably holding said arms in an engagement with said plunger rod.

11. The medicament delivery device according to claim 8, wherein the actuator is arranged with third engagement elements arranged to releasably engage said second engagement elements of said plunger rod.

12. The medicament delivery device according to claim 11, wherein said actuator is operably connected to an activator for activating said drive unit.

13. The medicament delivery device according to claim 12, wherein said activator comprises a medicament delivery member guard extending from a proximal end of the medicament delivery device and movable from an initial position to an activation position.

14. An assembly for advancing a medicament container within a housing of a medicament delivery device comprising:
a medicament container movable between a retracted position and an extended position and coaxial to a longitudinal axis of the housing, where the medicament container comprises a syringe barrel having a radially extending flange having a distal end surface;
a rear end cover configured to connect to an open distal end of the housing such that the rear end cover is axially fixed relative to the longitudinal axis, where when the rear end cover is connected to the housing the assembly is attached within the housing, and where the rear end cover has an internal portion comprising a radially inward extending flange;
an actuator having distal end and comprising a longitudinal groove that is in sliding engagement with the radially inward extending flange such that when the rear end cover is attached to the housing the actuator is rotationally fixed relative to the housing;
a medicament container holder for carrying the medicament container between the retracted position and the extended position, where the medicament container holder comprises a proximal end having a support surface;
a drive unit operatively engaged with the medicament container holder to move the medicament container from the retracted position to the extended position; and
a holding member releasably connected to the drive unit and attached to the medicament container holder, where the holding member comprises a biasing element having a proximal end surface that engages with and biases the distal end surface of the radially extending flange, where the drive unit biases the biasing element proximally such that the medicament container is biased in a proximal direction to cause the medicament container holder to abut the support surface,
wherein during medicament delivery member penetration the biasing element dampens the biasing force of the drive unit exerted upon the distal end surface of the medicament container to prevent breakage of the medicament container, and
wherein the biasing element comprises a resilient structure in the form of a tubular wall provided with slots extending in the generally circumferential direction.

15. The assembly according to claim 14, wherein the tubular wall is arranged with a first set of slots, where each slot extends a part of the circumference of the tubular wall, forming a bridge between each successive slot.

16. The medicament delivery device according to claim 15, wherein the tubular wall further is provided with second set of slots that each extend a part of the circumference of the tubular wall, forming a bridge between each successive slot, where the second set of slots is placed offset to the first set of slots as seen in a longitudinal direction.

17. The medicament delivery device according to claim 14, wherein said holding element is arranged with a number of distally directed arms having free ends.

18. The medicament delivery device according to claim 17, wherein the free ends of the arms are arranged with first engagement elements that releasably engage corresponding second engagement elements of a plunger rod of said drive unit.

19. A medicament delivery device comprising:
a medicament container comprising a syringe barrel having an attached medicament delivery member and a radially extending flange having a distal end surface;
a housing having a longitudinal axis and adapted to receive the medicament container, the medicament container being movable between a retracted position in which the medicament delivery member is contained within the housing and an extended position in which the medicament delivery member extends from the housing;
a rear end cover axially fixed relative to the longitudinal axis of the housing and fixedly attached to an open distal end of the housing, where the rear end cover comprises a guide post having an internal portion comprising an end wall and a radially inward extending curved flange;
an actuator having distal end wall and comprising a longitudinal groove that is in sliding engagement with and configured to match the curve of the radially inward extending curved flange such that distal end wall will engage with the end wall of the rear end cover as the actuator slides axially relative to the rear end cover when delivery of medicament from the medicament container is completed, where a distal portion of the actuator comprises a tubular guide element having a radially flexible proximally directed arm comprising a protrusion that is engaged with a longitudinally extending slit on the internal portion of the guide post;

a drive unit that acts upon the medicament container to advance it from its retracted position to its extended position and to expel its contents through the medicament delivery member; and a medicament container holder for carrying the medicament container as it is advanced, the medicament container holder having a proximal end that comprises a support surface and is configured with a through hole through which the medicament delivery member extends and a distal end opposite the proximal end; and a holding member releasably connected to the drive unit and attached to the medicament container holder, where the drive unit exerts a biasing force that moves the holding member proximally when the holding member is attached to the drive unit, wherein the holding member comprises, at its proximal end, a biasing element having a proximal end surface that engages with and biases the distal end surface of the radially extending flange, where the drive unit biases the biasing element proximally so as to bias the medicament container in a proximal direction within the medicament container holder such that the medicament container abuts the support surface so that the medicament container and the medicament container holder are axially fixed relative to each other, wherein during medicament delivery member penetration the biasing element dampens the biasing force of the drive unit exerted upon the distal end surface of the medicament container to prevent breakage of the medicament container, and wherein the biasing element comprises a resilient structure in the form of a tubular wall provided with slots extending in the generally circumferential direction.

* * * * *